(12) United States Patent
Angle et al.

(10) Patent No.: US 10,591,951 B2
(45) Date of Patent: *Mar. 17, 2020

(54) TRANSDUCER CLOCK SIGNAL DISTRIBUTION

(71) Applicant: uBeam Inc., Santa Monica, CA (US)

(72) Inventors: Matthew Angle, Cambridge, MA (US); Marc Berte, Ashburn, VA (US)

(73) Assignee: uBeam Inc., Marina del Rey, CA (US)

( * ) Notice: Subject to any disclaimer, the term of this patent is extended or adjusted under 35 U.S.C. 154(b) by 16 days.

This patent is subject to a terminal disclaimer.

(21) Appl. No.: 15/962,696

(22) Filed: Apr. 25, 2018

(65) Prior Publication Data

US 2018/0246540 A1    Aug. 30, 2018

Related U.S. Application Data

(63) Continuation of application No. 13/834,323, filed on Mar. 15, 2013, now Pat. No. 9,983,616.

(51) Int. Cl.
*G06F 1/10* (2006.01)
*A61B 8/00* (2006.01)

(52) U.S. Cl.
CPC .......... *G06F 1/10* (2013.01); *A61B 8/44* (2013.01); *A61B 8/4444* (2013.01)

(58) Field of Classification Search
CPC ............ A61B 8/44; A61B 8/4444; G06F 1/10
See application file for complete search history.

(56) References Cited

U.S. PATENT DOCUMENTS

| | | | |
|---|---|---|---|
| 3,946,831 | A  | 3/1976  | Bouyoucos |
| 6,037,704 | A  | 3/2000  | Welle |
| 6,127,942 | A  | 10/2000 | Welle |
| 6,445,108 | B1 | 9/2002  | Takeshima |
| 6,798,716 | B1 | 9/2004  | Charych |
| 7,489,967 | B2 | 2/2009  | Von Arx |
| 7,606,621 | B2 | 10/2009 | Brisken |
| 7,610,092 | B2 | 10/2009 | Cowan |
| 7,902,943 | B2 | 3/2011  | Sherrit |
| 8,082,041 | B1 | 12/2011 | Radziemski |
| 8,159,364 | B2 | 4/2012  | Zeine |
| 8,649,875 | B2 | 2/2014  | Sarvazyan |

(Continued)

FOREIGN PATENT DOCUMENTS

| | | |
|---|---|---|
| CN | 102184729 A  | 9/2011 |
| JP | H07327299 A  | 12/1995 |

(Continued)

OTHER PUBLICATIONS

Extended European Search Report dated Nov. 11, 2016 as received in Application No. 14764350.6.

(Continued)

*Primary Examiner* — Terrell S Johnson
(74) *Attorney, Agent, or Firm* — Morris & Kamlay LLP

(57) ABSTRACT

An array of ultrasonic transducers can be controlled to produce a steerable beam. Beam steering can be skewed by buffer delays in the distribution of a clock signal. The skew can be at least approximately linearized by distributing the clock signal in a diagonal fashion across an array of buffers corresponding to ultrasonic transducer controllers. Potential error in beam steering that can arise from clock skew can be corrected based on the linear tilt.

20 Claims, 2 Drawing Sheets

(56) References Cited

U.S. PATENT DOCUMENTS

| | | | |
|---|---|---|---|
| 9,983,616 B2* | 5/2018 | Angle | G06F 1/10 |
| 2001/0035700 A1 | 11/2001 | Percin | |
| 2003/0011285 A1 | 1/2003 | Ossmann | |
| 2003/0020376 A1 | 1/2003 | Sakaguchi | |
| 2004/0066708 A1 | 4/2004 | Ogawa | |
| 2004/0172083 A1 | 9/2004 | Penner | |
| 2004/0204744 A1 | 10/2004 | Penner | |
| 2005/0070962 A1 | 3/2005 | Echt | |
| 2005/0207589 A1 | 9/2005 | Biegelsen | |
| 2007/0109064 A1 | 5/2007 | Micko | |
| 2007/0109121 A1 | 5/2007 | Cohen | |
| 2007/0150019 A1 | 6/2007 | Youker | |
| 2008/0184549 A1 | 8/2008 | Nguyen-Dinh | |
| 2008/0309452 A1 | 12/2008 | Zeine | |
| 2009/0016163 A1 | 1/2009 | Freeman | |
| 2010/0027379 A1 | 2/2010 | Saulnier | |
| 2010/0157019 A1 | 6/2010 | Schwotzer | |
| 2010/0164433 A1 | 7/2010 | Janefalkar | |
| 2010/0286744 A1 | 11/2010 | Echt | |
| 2010/0315045 A1 | 12/2010 | Zeine | |
| 2012/0071762 A1 | 3/2012 | Sato | |
| 2012/0193999 A1 | 8/2012 | Zeine | |
| 2012/0299540 A1 | 11/2012 | Perry | |
| 2012/0299541 A1 | 11/2012 | Perry | |
| 2012/0299542 A1 | 11/2012 | Perry | |
| 2012/0300588 A1 | 11/2012 | Perry | |
| 2012/0300592 A1 | 11/2012 | Perry | |
| 2012/0300593 A1 | 11/2012 | Perry | |
| 2013/0069865 A1 | 3/2013 | Hart | |
| 2013/0207604 A1 | 8/2013 | Zeine | |
| 2013/0241468 A1 | 9/2013 | Moshfeghi | |
| 2013/0271088 A1 | 10/2013 | Hwang | |
| 2014/0243676 A1 | 8/2014 | Cogan | |

FOREIGN PATENT DOCUMENTS

| | | |
|---|---|---|
| JP | 2008244964 A | 10/2008 |
| KR | 20090118873 | 11/2009 |
| WO | 0021020 A2 | 4/2000 |
| WO | 2006069215 A2 | 6/2006 |
| WO | 2012166583 A1 | 12/2012 |

OTHER PUBLICATIONS

Invitation to Pay Additional Fees and Partial International Search Report for PCT/US2014/028133 dated Jul. 18, 2014.

Bao, et al., "High-power piezoelectric acoustic-electric power feedthru for metal walls", Proceedings of SPIE, vol. 6930, pp. 1-8, 2008.

Bao, et al., "Wireless piezoelectric acoustic-electric power feedthru", Proceedings of SPIE, vol. 6529, pp. 1-7, 2007.

Etherington, "Cota by Ossia Aims to Drive a Wireless Power Revolution and Change How We Think About Charging", Available at: http://techcrunch.com/2013/09/09/cota-by-ossia-wireless-power/. Date visited: Sep. 12, 2013, pp. 1-4, Sep. 9, 2013.

Mobilitywire, "Ossia Unveils World's First Commercially Viable Remote Wireless Power System", Available at: http://www.mobilitywire.com/ossia/2013/09/10/7888. Date visited: Sep. 12, 2013, pp. 1-4, Sep. 10, 2013.

Sherrit, et al., "Comparison of the Mason and KLM Equivalent Circuits for Piezoelectric Resonators in the Thickness Mode", IEEE Ultrasonics Symposium, vol. 2, pp. 921-926, 1999.

Sherrit, et al., "Efficient Electromechanical Network Models for Wireless Acoustic-Electric Feed-throughs", Proceedings of the SPIE Smart Structures Conference, vol. 5758, pp. 362-372, Mar. 6-10, 2005.

Sherrit, et al., "Solid Micro Horn Array (SMIHA) for Acoustic Matching", Proceedings of SPIE, vol. 6932, pp. 1-9, 2008.

Sherrit, et al., "Studies of Acoustic-Electric Feed-throughs for Power Transmission Through Structures", Proceedings of SPIE, vol. 6171, pp. 1-8, 2006.

Sherrit, "The Physical Acoustics of Energy Harvesting", IEEE International Ultrasonics Symposium Proceedings, pp. 1046-1055, 2008.

Germano, "Flexure Mode Piezoelectric Transducers", Morgan Electro Ceramics, Technical Publication TP-218. J. Accoust. Soc. Am. vol. 50, Issue 1A, pp. 1-6, 1971.

International Search Report, "in International Application No. PCT/US2012/039536" dated Aug. 14, 2012.

Morgan Electro Ceramics, "Cantilever Mounted PZT 5A Bimorphs", Technical Publication TP-245, pp. 1-8, 1999.

Intellectual Ventures, "MSA-T", Available at: http://www.intellectualventures.com/index.php/inventions-patents/our-inventions/msa-t. Date visited: Mar. 21, 2013.

Intellectual Ventures, "MSA-T: Enabling . . . " http://www.intellectualventures.com/assets_docs/IV_metamaterials_technical_overview.pdf. Mar. 21, 2013.

Notice of Allowance dated Feb. 27, 2018 for U.S. Appl. No. 13/834,323; (pp. 1-5).

* cited by examiner

TRANSDUCER CLOCK SIGNAL DISTRIBUTION

BACKGROUND

Ultrasonic transducers receive electrical energy as an input and provide acoustic energy at ultrasonic frequencies as an output. An ultrasonic transducer can be a piece of piezoelectric material that changes size in response to the application of an electric field. If the electric field is made to change at a rate comparable to ultrasonic frequencies, then the piezoelectric element can vibrate, causing it to generate ultrasonic frequency acoustic waves.

BRIEF SUMMARY

An array of ultrasonic transducers can be controlled by a set of controllers. Each controller can have a corresponding buffer. A first controller buffer can receive a clock signal and send it to second and third controller buffers. The second controller buffer can be horizontally adjacent to the first controller buffer. The third board controller buffer can be vertically adjacent to the first controller buffer. The second and third controller buffers can further distribute the clock signal to horizontally and vertically controller buffers, respectively.

A clock skew can be determined based on the buffer delays and/or propagation delays in distributing the clock signal. A tilt can be determined based on the determined clock skew. A beam steering command can be corrected for the determined tilt.

BRIEF DESCRIPTION OF THE DRAWINGS

The accompanying drawings, which are included to provide a further understanding of the disclosed subject matter, are incorporated in and constitute a part of this specification. The drawings also illustrate implementations of the disclosed subject matter and together with the detailed description serve to explain the principles of implementations of the disclosed subject matter. No attempt is made to show structural details in more detail than may be necessary for a fundamental understanding of the disclosed subject matter and various ways in which it may be practiced.

DETAILED DESCRIPTION

An implementation in accordance with the present disclosure can include an array of ultrasonic transducers at a transmitter. The transducers can be caused to vibrate as a phased array to form a steerable beam of ultrasonic acoustic energy. The steerable beam can be directed to a receiver. The receiver can convert received ultrasonic acoustic energy to electrical energy. The rate of power transfer can depend at least partly on the shape of the beam and the accuracy with which the beam can be steered by the transmitter to the receiver.

The transducers can be controlled by a system that is arranged in a hierarchical architecture. For example, an array of ultrasonic transducers (a "tile") can be controlled by a tile controller. A controller can refer to a general purpose microprocessor, an Application Specific Integrated Circuit or any suitable electronic control system. A controller can include a buffer that store and/or amplify a clock signal. An array of tiles can be arranged in one or more subarrays. A subarray can be controlled by a subarray controller. One or more subarrays can be arranged in a board. A board can be controlled by a board controller. One or more boards can be arranged in a board array that can be controlled by a board array controller, and so on. Each controller can have a clock signal supplied by a local buffer.

Figure 1:
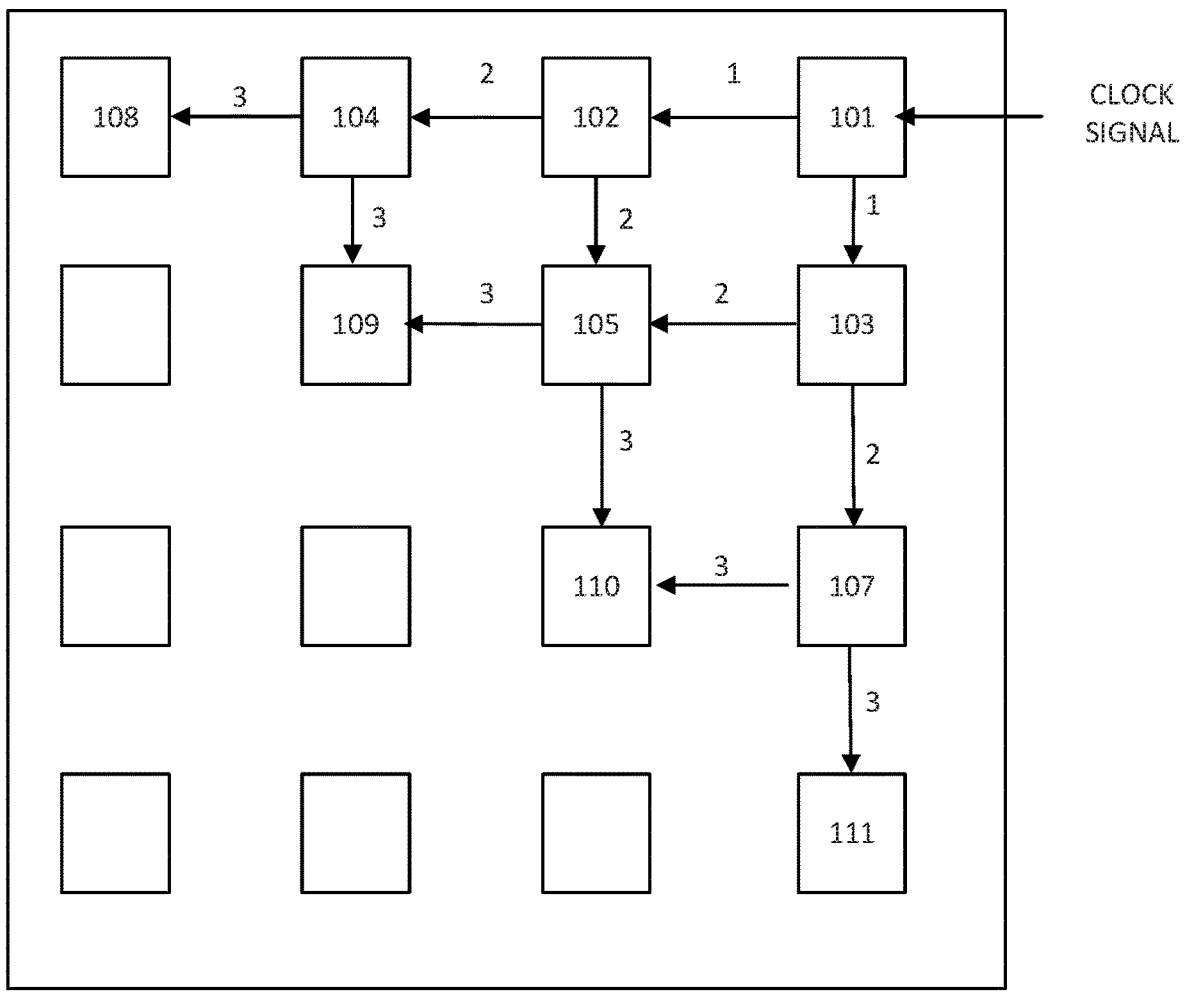
FIG. 1 shows a distribution of a clock signal among board buffers according to an implementation of the disclosed subject matter.

For an implementation such as that shown in FIG. 1, a clock signal can be received from a board array controller buffer (not shown) at a board controller buffer 101. The clock signal can be received at a second board controller buffer 102 and a third board controller buffer 103 at substantially the same time. As shown in FIG. 1, the second board controller buffer 102 can be horizontally adjacent to the first board controller buffer 101 and the third board controller buffer 103 can be vertically adjacent to the first board controller buffer 101.

The clock signal can then be received from the second board controller buffer 102 at a fourth board controller buffer 104 and a fifth board controller buffer 105. The fourth board controller buffer can be horizontally adjacent to the second board controller buffer and the fifth board controller buffer can be vertically adjacent to the second board controller buffer 102. Likewise, the clock signal received at the third board controller buffer 103 can be received by a seventh board controller buffer 107. Optionally, the clock signal can also be received from the third board controller buffer 103 at the fifth board controller buffer 105. The fifth board controller buffer 105 can buffer the first of the clock signals received from the second board controller buffer 102 and the third board controller buffer. In an implementation, the fifth board controller buffer can average the clock signals received from the second board controller buffer 102 and the third board controller buffer 103. In an implementation, the fifth board controller buffer 105 can buffer the last of the clock signals received from the second board controller buffer 102 and the third board controller buffer 103. The third board controller buffer can treat the two clock signals in any suitable way.

In like fashion, each board-level buffer can send the clock signal to the board-level buffers to which it is horizontally adjacent and vertically adjacent, for example 108-111 as shown in FIG. 1. An adjacent board controller buffer to which a sending board controller buffer sends a clock signal can be one that has not yet received the clock signal.

The disclosed implementations for distributing the clock signal across buffers can render the delay in clock skew across the boards approximately linear. The resulting tilt in the array due to clock skew can be a linear tilt. It can be simpler to compensate for a linear tilt than a nonlinear tilt. For example, it can be relatively straightforward to determine the tilt angle based on the delay properties of the buffers. A known tilt angle can be corrected by adjusting the beam steering accordingly. This can enable a controller to more accurately steer the beam, which can result in more accurate and efficient power transfer from an ultrasonic power transmitter to a ultrasonic power receiver.

In an implementation, a clock signal that is received at a board controller buffer can be propagated at substantially the same time to the subarray controller buffers for subarray controllers that are controlled by the board controller. A subarray controller buffer can further distribute the clock signal at substantially the same time to the tile controller buffers for tile controllers that are controlled by the subarray controller. In this way, clock signals can be propagated down the hierarchy of buffers in an orderly way. The diagonal propagation of the clock signal across the board controller buffers can linearize clock skew and make it easier to compensate for tilt that arises from buffer and other delays in clock signal distribution.

In an implementation, the clock signal is distributed by a board controller buffer to corresponding subarray controller buffers in the same way as the clock signal is distributed among the board controller buffers. For example, the clock signal can be received by a first subarray controller buffer and be distributed substantially at the same time to second and third subarray controller buffers, where the second subarray controller buffer is horizontally adjacent to the first subarray controller buffer and the third subarray controller buffer is vertically adjacent to the first subarray controller buffer. Each of the second and third subarray controller buffers can further distribute the clock signal as the second and third board controllers distribute the clock signal.

Similarly, a subarray controller buffer can distribute the clock signal to corresponding tile controllers. This can be done in the same way at the tile controller buffer level as described above for the subarray controller buffers and for the board controller buffers.

Any suitable hierarchy can be used to distribute a clock signal in accordance with the disclosed subject matter. For example, in an implementation, the clock signal can be distributed as shown in FIG. 1 directly to subarray controller buffers. In such a case, there may or may not be a board controller level. Likewise, the clock signal can be similarly distributed directly to tile controller buffers. In that case, there may or may not be subarray or board level controllers. If there are only tile controllers, the hierarchy can have only a single level.

Known or measure buffer delays in distributing the clock signal can be used to determine clock skew. Determined clock skew can be used to determine tilt in beam steering caused by the buffer delays. Steering commands to the system can be changed to compensate for the determined tilt. For example, if the determined tilt includes a −3 degree tilt in azimuth, then the steering commands can be adjusted to add a +3 degree change in azimuthal beam direction when steering the beam from the transmitter to the receiver.

Figure 2:
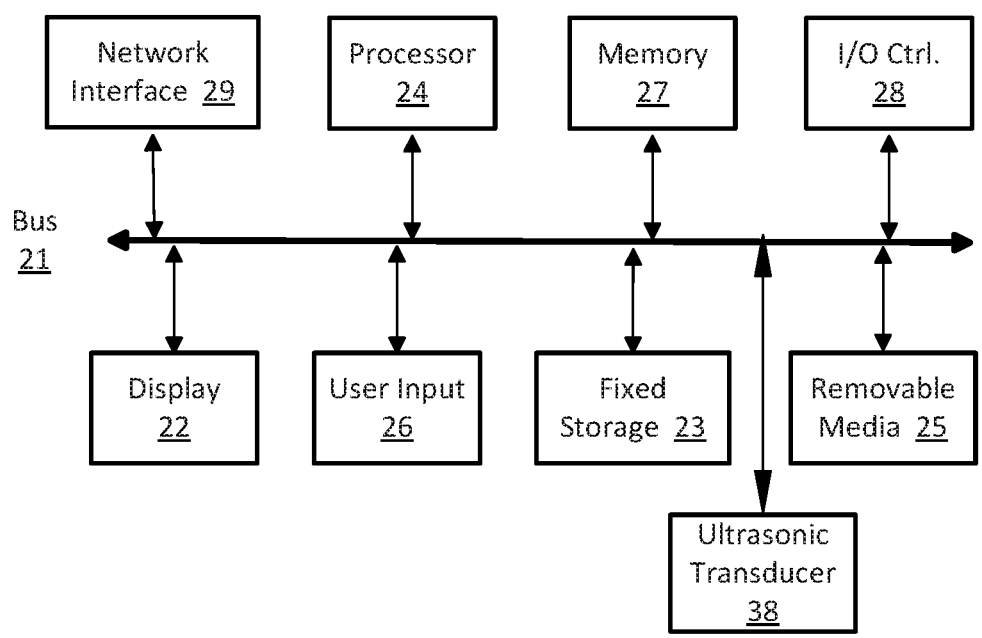
FIG. 2 shows a computer according to an implementation of the disclosed subject matter.

Implementations of the presently disclosed subject matter may be implemented in and used with a variety of component and network architectures. FIG. 2 is an example computer 20 suitable for implementations of the presently disclosed subject matter. The computer 20 includes a bus 21 which interconnects major components of the computer 20, such as a central processor 24, a memory 27 (typically RAM, but which may also include ROM, flash RAM, or the like), an input/output controller buffer 28, a user display 22, such as a display screen via a display adapter, a user input interface 26, which may include one or more controller buffers and associated user input devices such as a keyboard, mouse, and the like, and may be closely coupled to the I/O controller buffer 28, fixed storage 23, such as a hard drive, flash storage, Fibre Channel network, SAN device, SCSI device, and the like, and a removable media component 25 operative to control and receive an optical disk, flash drive, and the like. Memory 27 can include a buffer. Processor 24 can correspond to a controller.

The bus 21 allows data communication between the central processor 24 and the memory 27, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components. Applications resident with the computer 20 are generally stored on and accessed via a computer readable medium, such as a hard disk drive (e.g., fixed storage 23), an optical drive, floppy disk, or other storage medium 25. The bus 21 also allows communication between the central processor 24 and the ultrasonic transducer 38. For example, data can be transmitted from the processor 24 to a waveform generator subsystem (not shown) to form the control signal that can drive the ultrasonic transducer 39.

The fixed storage 23 may be integral with the computer 20 or may be separate and accessed through other interfaces. A network interface 29 may provide a direct connection to a remote server via a telephone link, to the Internet via an internet service provider (ISP), or a direct connection to a remote server via a direct network link to the Internet via a POP (point of presence) or other technique. The network interface 29 may provide such connection using wireless techniques, including digital cellular telephone connection, Cellular Digital Packet Data (CDPD) connection, digital satellite data connection or the like. For example, the network interface 29 may allow the computer to communicate with other computers via one or more local, wide-area, or other networks, as shown in FIG. 3.

Many other devices or components (not shown) may be connected in a similar manner. Conversely, all of the components shown in FIG. 2 need not be present to practice the present disclosure. The components can be interconnected in different ways from that shown. The operation of a computer such as that shown in FIG. 2 is readily known in the art and is not discussed in detail in this application. Code to implement the present disclosure can be stored in computer-readable storage media such as one or more of the memory 27, fixed storage 23, removable media 25, or on a remote storage location. For example, such code can be used to provide the waveform and other aspects of the control signal that drives a flexure.

Figure 3:
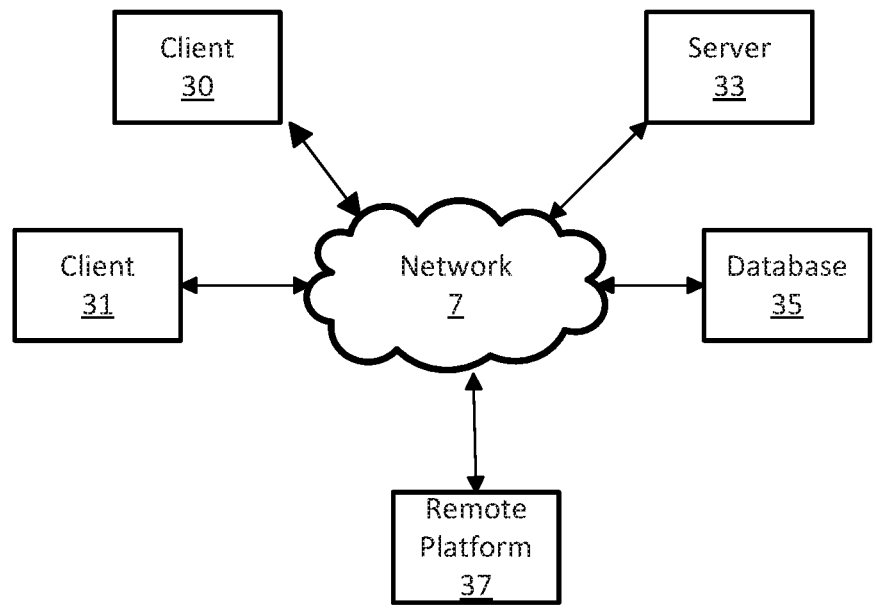
FIG. 3 shows a network configuration according to an implementation of the disclosed subject matter.

FIG. 3 shows an example network arrangement according to an implementation of the disclosed subject matter. One or more clients 10, 11, such as local computers, smart phones, tablet computing devices, and the like may connect to other devices via one or more networks 7. The network may be a local network, wide-area network, the Internet, or any other suitable communication network or networks, and may be implemented on any suitable platform including wired and/or wireless networks. The clients may communicate with one or more servers 13 and/or databases 15. The devices may be directly accessible by the clients 10, 11, or one or more other devices may provide intermediary access such as where a server 13 provides access to resources stored in a database 15. The clients 10, 11 also may access remote platforms 17 or services provided by remote platforms 17 such as cloud computing arrangements and services. The remote platform 17 may include one or more servers 13 and/or databases 15.

More generally, various implementations of the presently disclosed subject matter may include or be implemented in the form of computer-implemented processes and apparatuses for practicing those processes. Implementations also may be implemented in the form of a computer program product having computer program code containing instructions implemented in non-transitory and/or tangible media, such as floppy diskettes, CD-ROMs, hard drives, USB (universal serial bus) drives, or any other machine readable storage medium, wherein, when the computer program code is loaded into and executed by a computer, the computer becomes an apparatus for practicing implementations of the disclosed subject matter. Implementations also may be implemented in the form of computer program code, for example, whether stored in a storage medium, loaded into and/or executed by a computer, or transmitted over some transmission medium, such as over electrical wiring or cabling, through fiber optics, or via electromagnetic radiation, wherein when the computer program code is loaded into and executed by a computer, the computer becomes an apparatus for practicing implementations of the disclosed subject matter. When implemented on a general-purpose microprocessor, the computer program code segments configure the microprocessor to create specific logic circuits. In some configurations, a set of computer-readable instructions stored on a computer-readable storage medium may be implemented by a general-purpose processor, which may transform the general-purpose processor or a device containing the general-purpose processor into a special-purpose device configured to implement or carry out the instructions. Implementations may be implemented using hardware that may include a processor, such as a general purpose microprocessor and/or an Application Specific Integrated Circuit (ASIC) that implements all or part of the techniques according to implementations of the disclosed subject matter in hardware and/or firmware. The processor may be coupled to memory, such as RAM, ROM, flash memory, a hard disk or any other device capable of storing electronic information. The memory may store instructions adapted to be executed by the processor to perform the techniques according to implementations of the disclosed subject matter.

The foregoing description, for purpose of explanation, has been described with reference to specific implementations. However, the illustrative discussions above are not intended to be exhaustive or to limit implementations of the disclosed subject matter to the precise forms disclosed. Many modifications and variations are possible in view of the above teachings. The implementations were chosen and described in order to explain the principles of implementations of the disclosed subject matter and their practical applications, to thereby enable others skilled in the art to utilize those implementations as well as various implementations with various modifications as may be suited to the particular use contemplated.

The invention claimed is:

1. A method, comprising:
 receiving a clock signal at a first tile controller buffer of a plurality of tile controller buffers;
 receiving the clock signal received at the first tile controller buffer at a second tile controller buffer and a third tile controller buffer at substantially the same time from the first tile controller buffer, the second tile controller buffer being horizontally adjacent to the first tile controller buffer and the third tile controller buffer being vertically adjacent to the first tile controller buffer; and
 receiving the clock signal received at the first tile controller buffer at a fourth controller buffer from the first tile controller buffer and the clock signal received at the second tile controller buffer at the fourth tile controller buffer, the fourth tile controller buffer being horizontally adjacent to the third tile controller buffer and vertically adjacent to the second tile controller buffer.

2. The method of claim 1, wherein the second tile controller buffer has not yet received the clock signal at the time it receives the clock signal from the first tile controller buffer.

3. The method of claim 1, wherein the third tile controller buffer has not yet received the clock signal at the time it receives the clock signal from the first tile controller buffer.

4. The method of claim 1, wherein the clock signal is received at the first tile controller buffer from a first subarray controller buffer.

5. The method of claim 4, wherein the clock signal is received at the first subarray controller buffer from a first board controller buffer.

6. The method of claim 1, further comprising receiving the clock signal at an ultrasonic transducer of a first tile of ultrasonic transducers from the first tile controller buffer.

7. The method of claim 1, further comprising determining a clock skew.

8. The method of claim 7, further comprising determining a tilt based on the determined clock skew.

9. The method of claim 8, further comprising correcting a beam steering command based on the determined tilt.

10. A system, comprising:
 a plurality of tile controller buffers;
 a clock signal generator; and
 a computer-implemented clock signal distributor that sends a clock signal from a first tile controller buffer of the plurality of tile controller buffers at substantially the same time to a second tile controller buffer and third tile controller buffer, the second tile controller buffer being horizontally adjacent to the first tile controller buffer and the third tile controller buffer being vertically adjacent to the first tile controller buffer, sends a clock signal received from the first tile controller buffer at the second tile controller buffer to a fourth tile controller buffer from the second tile controller buffer, the fourth tile controller buffer being vertically adjacent to the second tile controller buffer and horizontally adjacent to the third tile controller buffer, and sends a clock signal received from the first tile controller buffer at the third tile controller buffer to the fourth tile controller buffer from the third tile controller buffer.

11. The system of claim 10, wherein a first tile comprises the first tile controller buffer and a plurality of ultrasonic transducers.

12. The system of claim 11, wherein the first tile controller buffer sends the clock signal to at least one of the plurality of ultrasonic transducers of the first tile.

13. The method of claim 10, wherein a clock skew is determined.

14. The method of claim 13, wherein a tilt is determined based on the clock skew.

15. The method of claim 14, wherein a beam steering command sent to at least one tile comprising ultrasonic transducers is corrected based on the tilt.

16. A method, comprising:
 receiving a clock signal at a first tile controller buffer of a plurality of tile controller buffers;
 receiving the clock signal received at the first tile controller buffer at a second tile controller buffer and a third tile controller buffer at substantially the same time from the first tile controller buffer, the second tile controller buffer being horizontally adjacent to the first tile controller buffer and the third tile controller buffer being vertically adjacent to the first tile controller buffer; and receiving the clock signal received at the first tile controller buffer at a fourth controller buffer from the first tile controller buffer and the clock signal received at the second tile controller buffer at the fourth tile controller buffer, the fourth tile controller buffer being horizontally adjacent to the third tile controller buffer and vertically adjacent to the second tile controller buffer.

17. A method, comprising:

receiving a clock signal at a first subarray controller buffer of a plurality of subarray controller buffers;

receiving the clock signal received at the first subarray controller buffer at a second subarray controller buffer and a third subarray controller buffer at substantially the same time from the first subarray controller buffer, the second subarray controller buffer being horizontally adjacent to the first subarray controller buffer and the third subarray controller buffer being vertically adjacent to the first subarray controller buffer; and receiving the clock signal received at the first subarray controller buffer at a fourth controller buffer from the first subarray controller buffer and the clock signal received at the second subarray controller buffer at the fourth subarray controller buffer, the fourth subarray controller buffer being horizontally adjacent to the third subarray controller buffer and vertically adjacent to the second subarray controller buffer.

18. The method of claim 17, further comprising receiving the clock signal at a first tile controller buffer from the first subarray controller buffer.

19. The method of claim 18, further comprising receiving the clock signal at an ultrasonic transducer of a tile from the first tile controller buffer.

20. The method of claim 18, further comprising receiving the clock signal a second tile controller buffer from the first tile controller buffer.

* * * * *